(12) United States Patent
Palmer et al.

(10) Patent No.: US 10,488,356 B2
(45) Date of Patent: Nov. 26, 2019

(54) METHOD FOR PRODUCING AN ELECTRICAL IMPEDANCE TOMOGRAPHIC IMAGE OF AN ACOUSTIC FIELD AND A SYSTEM FOR PERFORMING SAID METHOD

(71) Applicant: TTP PLC, Royston (GB)

(72) Inventors: Timothy John Palmer, Royston (GB);
Edward Leigh Bean, Royston (GB);
David Roger Tegerdine, Royston (GB)

(73) Assignee: TTP PLC (GB)

( * ) Notice: Subject to any disclaimer, the term of this patent is extended or adjusted under 35 U.S.C. 154(b) by 50 days.

(21) Appl. No.: 15/548,642

(22) PCT Filed: Feb. 5, 2016

(86) PCT No.: PCT/GB2016/050275
§ 371 (c)(1),
(2) Date: Aug. 3, 2017

(87) PCT Pub. No.: WO2016/124945
PCT Pub. Date: Aug. 11, 2016

(65) Prior Publication Data
US 2018/0003658 A1 Jan. 4, 2018

(30) Foreign Application Priority Data
Feb. 5, 2015 (GB) .................. 1501891.4

(51) Int. Cl.
*G01R 27/02* (2006.01)
*G01N 27/02* (2006.01)
*G01H 11/06* (2006.01)
*G01H 3/12* (2006.01)

(52) U.S. Cl.
CPC ........... *G01N 27/026* (2013.01); *G01H 3/125* (2013.01); *G01H 11/06* (2013.01)

(58) Field of Classification Search
CPC ...... G01N 27/02; G01N 27/026; G01N 27/22; G01N 27/226; G01N 27/20; G01N 27/24;
(Continued)

(56) References Cited

U.S. PATENT DOCUMENTS 2,411,117 A   11/1946 Scherbatskoy
4,539,640 A    9/1985 Fry et al.
(Continued)

FOREIGN PATENT DOCUMENTS

GB    2457587 A    8/2009
WO    2014066494 A1    5/2014
(Continued)

OTHER PUBLICATIONS

A. Wexler, B. Fry, and M. R. Neuman, entitled "Impedance-Computed Tomography Algorithm and System," Applied Optics. vol. 24, No. 23, pp. 3985-3992.
(Continued)

*Primary Examiner* — Thang X Le
(74) *Attorney, Agent, or Firm* — Lerner, David, Littenberg, Krumholz & Mentlik, LLP

(57) ABSTRACT

There is provided A method for producing an electrical impedance tomographic image of an acoustic field within a fluid, comprising the steps of: a) positioning a plurality of electrodes within a fluid; b) applying an electrical signal to each electrode within a first subset of electrodes, wherein the electrical signal applied to each electrode has a different carrier frequency and/or phase; c) measuring the electrical potential at each electrode within a second subset of electrodes; and d) processing the measured data to provide an acoustic map of the acoustic field at the required acoustic frequencies. There is also provided a system for producing an electrical impedance tomographic image of an acoustic field within a fluid using the method of any preceding claim, (Continued)

comprising a plurality of electrodes, a signal generator adapted to perform step (b), a device adapted to perform step (c), and a processor adapted to perform step (d).

20 Claims, 2 Drawing Sheets

(58) Field of Classification Search
CPC .............. G01N 27/08; G01N 2291/011; G01N 2291/02433; G01N 2291/024; G01N 2291/02863; A61B 5/053; A61B 5/0536; A61B 5/4064; A61B 8/485; G01R 27/28; G01B 15/06; G01F 1/586; G01F 1/584; G01F 1/588
See application file for complete search history.

(56) References Cited

U.S. PATENT DOCUMENTS

| | | | | |
|---|---|---|---|---|
| 2004/0242989 | A1* | 12/2004 | Zhu | A61B 5/0536 600/407 |
| 2010/0007357 | A1 | 1/2010 | Ammari et al. | |
| 2012/0098549 | A1* | 4/2012 | Wang | G01N 27/026 324/649 |
| 2013/0049770 | A1* | 2/2013 | Basu | G01N 27/026 324/654 |
| 2015/0020579 | A1* | 1/2015 | Kersey | G01N 27/06 73/61.41 |
| 2015/0346129 | A1* | 12/2015 | Kersey | G01B 15/06 324/701 |

FOREIGN PATENT DOCUMENTS

| WO | 2015009251 A1 | 1/2015 |
|---|---|---|
| WO | 2016030717 A1 | 3/2016 |
| WO | 2018025031 A1 | 2/2018 |

OTHER PUBLICATIONS

H. Ammari et al., "Electrical Impedance Tomography by Elastic Deformation," SIAM Journal on Applied Mathmatics, vol. 68, No. 6, Jan. 1, 2008 (Jan. 1, 2008), pp. 1557-1573, XP055412081.
Search Report from International Application No. PCT/GB2016/050275, dated May 9, 2016.

* cited by examiner

METHOD FOR PRODUCING AN ELECTRICAL IMPEDANCE TOMOGRAPHIC IMAGE OF AN ACOUSTIC FIELD AND A SYSTEM FOR PERFORMING SAID METHOD

CROSS-REFERENCE TO RELATED APPLICATIONS

The present application is a national phase entry under 35 U.S.C. § 371 of International Application No. PCT/GB2016/050275 filed Feb. 5, 2016, published as International Publication No. WO 2016/124945 A1, which claims priority from Great Britain Application No. 1501891.4 filed Feb. 5, 2015, all of which are incorporated herein by reference.

FIELD

The present invention relates to improved methods of detecting acoustic waves in fluids and has applications within SONAR. It can specifically aid in the detection of 3D acoustic wave fields, which also has applications for the control of noise, acoustic emissions and for object detection and ranging.

BACKGROUND

Electrical Impedance Tomography (EIT) is an imaging methodology that is based upon electrical conductivity or impedance contrasts within an object. U.S. Pat. No. 4,539,640, issued Sep. 3, 1995, to inventors Bradley Fry and Alvin Wexler, and the article by A. Wexler, B. Fry and M. R. Neuman, entitled "Impedance-Computed Tomography: Algorithm And System", Applied Optics, Vol. 24, No. 23, pp. 3985-3992, describe a method and embodiment of a system that solved electromagnetic field equations that govern current flow in a conductive medium, and concurrently extracted an image of the interior of the medium based on the electric current conductivity (and, more generally, specific impedance) distribution in the medium. This provided a methodology for the correct mathematical solution of the inverse (imaging) problem and construction of electronic equipment for this purpose.

Whilst EIT has frequently been applied to observe bulk changes in electrically heterogeneous media to detect relatively large changes in static objects, it does not allow for rapid detection of relatively small changes in the electrical impedance of a fluid.

Furthermore, existing acoustic sensing arrays can only provide a 2D slice or surface through the sound field, and as such cannot extend into the depth of the fluid to provide a 3D measurement. Whilst it would be possible to deploy a full 3D array of microphones, this array is likely to influence the sound field, and would require a large measurement array that protrudes into the depth of the fluid being imaged. This technique allows for detection at a distance away from the target.

SUMMARY

The object for the present invention is to provide measurements of the acoustic field in fluids, including 3D images of the sound field. In accordance with one aspect of the present invention, there is provided a: method for producing an electrical impedance tomographic image of an acoustic field within a fluid, comprising the steps of:

a) positioning a plurality of electrodes within a fluid;
b) applying an electrical signal to each electrode within a first subset of electrodes, wherein the electrical signal applied to each electrode has a different carrier frequency and/or phase;
c) measuring the electrical potential at each electrode within a second subset of electrodes;
and d) processing the measured data to provide an acoustic map of the acoustic field at the required acoustic frequencies.

The proposed method extends the concept of prior methods to allow for rapid detection of relatively small changes in the electrical impedance of a fluid caused by the changing density of an acoustic wave interacting with the electric field of a pair of electrodes. To detect acoustic frequencies, the carrier electrical signal should be greater than the acoustic frequency being observed.

A "subset" is preferably understood as a set of electrodes representing less than all of the plurality of electrodes. In a particular configuration of the present invention, the first subset of electrodes and the second subset of electrodes are mutually exclusive. Each subset could comprise any number of electrodes, including a single electrode, but preferably at least two electrodes (i.e. a plurality of electrodes).

It should be understood that the combination of the first and second subsets of electrodes may or may not be the total number of electrodes in the plurality of electrodes. For example, of a plurality of 20 electrodes, the first subset may comprise 4 electrodes and the second subset may comprise 4 electrodes. In another example, the plurality of electrodes may comprise 3 electrodes. However, in most preferred examples, all of the electrodes in the array are included in either the first or the second subset.

Preferably, in step (b), the electrical signal(s) may be applied substantially simultaneously to all of the electrodes in the first subset of electrodes. Additionally or alternatively, in step (c), the electrical potential at all of electrodes in the second subset of electrodes may be measured substantially simultaneously. This is advantageous in that this allows the method to be performed quicker than known methods, and this provides for rapid detection of changes in acoustic field in the fluid.

The method may further comprise calculating the electrical impedance between at least one pair of electrodes, and preferably between a plurality of pairs of electrodes, wherein a first electrode of the or each pair is selected from the first subset and a second electrode of the or each pair is selected from the second subset. By applying tomographic processing techniques to the measured electrical impedances, a 3-dimensional (3D) image of the acoustic or sound field can be produced.

Preferably, the method may further comprise repeating steps (b) and (c) over a different first and second subset of electrodes respectively. In this example, the electrodes of the different first and second subsets may include any of the plurality of electrodes. These may or may not include electrodes of the original first and second subset. In each configuration of different first and second subsets, the first and second subsets of electrodes are mutually exclusive.

Additionally or alternatively, the method may further comprise repeating steps (b) and (c) using different carrier frequencies and/or phases at step (b).

The impedance between electrodes may additionally be measured across a range of frequencies to compensate for global longer term trends in the electrical environment that are not related to the acoustic field, such as temperature, pressure, chemical composition, electrode composition and surface effects. Thus, at predetermined intervals, an apparatus that is used to perform the method of the present invention may be used to derive information about other certain parameters of the fluid in which it operates. This can be done by applying different (usually lower or a wider range of) frequencies between electrodes and measuring the impedance across certain electrode pairs. Preferably, the fluid may be represented as a component of an electrical model.

Yet more preferably, the derived information may be used to adjust step (d) of the method.

In an example of the present invention, the first and second subsets may each comprise only a single electrode and the electrical impedance is measured across the resulting electrode pair, to provide a 1 dimensional measurement of acoustic signal strength across the electrode pair, wherein the signal strength is a function of the measured electrical impedance.

Preferably, the electrodes may comprise conductive and non-corrosive materials such as carbon fibre.

Preferably, the electrodes may be positioned on a measurement surface and are flush or conformal to the surface. Advantageously, the electrodes may be closely spaced from one another.

Preferably, the different carrier frequencies and/or phases in step (b) may be selected such that the electrical properties of the measurement fluid either do not change significantly between the different carrier frequencies and/or phases, or that the change with frequency and/or phases is known.

In accordance with another aspect of the present invention, there is provided a system for producing an electrical impedance tomographic image of an acoustic field within a fluid using the method of any preceding claim, comprising a plurality of electrodes, a signal generator adapted to perform step (b), a device adapted to perform step (c), and a processor adapted to perform step (d).

The signal generator may be an electrical signal source. The device adapted to perform step (c) may be an electrical signal detector. The device adapted to perform step (c) may be further adapted to calculate the electrical impedance between at least one pair of electrodes, and preferably between a plurality of pairs of electrodes, wherein a first electrode of the or each pair is selected from the first subset and a second electrode of the or each pair is selected from the second subset. The processor adapted to perform step (d) may be a tomographic processor.

The carrier waves must be at a frequency that is greater than the acoustic wave of interest. Also, the stimulus and measurements steps and associated repeats must be carried out within the required sampling time in order to capture the acoustic wave. For example, if the highest required acoustic frequency of interest is 1000 Hz, then the absolute minimum sampling time to complete the stimulus and measurements steps and associated repeats must be less than 0.5 ms.

Rather than stimulating separately on each electrode at the same frequency as is common in EIT for the imaging of objects, to detect the acoustic wave within a suitable time step it is necessary to transmit simultaneously on different frequencies. For a given fluid, the electrical properties should either be the same across the range of frequencies used, or the change in electrical properties across the frequency range must be well known. Also, the relative phase may be varied instead/as well as the frequency.

As well as the generation of tomographic measurements, the acoustic field between a single pair of electrodes can be measured to provide a single 'point' acoustic field measurement as an alternative to existing hydrophone or acoustic measurement systems.

Changes in the fluid and electrode properties over time will result in a changing sensitivity to the sound field. By additionally measuring across a range of frequencies, it is possible to determine the equivalent electrical circuit of the electrodes and to identify and characterise: changes due to the electrodes (such as changes in surface properties, or temperature), changes due to the bulk fluid (such as chemical composition, temperature) and also changes due to the interface between the electrodes and the fluid such as the double layer effect. As each of these circuit elements can be affected differently by temperature, pressure, chemical composition, temperature, material properties and by inbound acoustic waves, the changes may be compensated for such that it is possible to calibrate for the absolute sound pressure level.

Short term changes in the sensing environment might also be detected using techniques both from Electrical Impedance Spectroscopy and Electrical Impedance Tomography. These may be used to provide detection and identification of non-acoustic articles and effects within the sensing volume of the fluid.

This technique is likely to work best on conductive fluids such as seawater. In a preferable example, the fluid may be a liquid such as seawater. Furthermore, this technique is likely to work best with electrodes that are highly conductive. However, there are other properties of the electrodes such as corrosion resistance and surface finish that will also influence the performance of the electrodes when used with a given fluid.

The system may provide directionality to the acoustic field (i.e. a greater sensitivity in a desired direction) either by shaping the electrodes or by manipulating the stimulating signal.

The electrodes may be configured in a variety of layouts to achieve directionality. In one example, each of the plurality of electrodes may be arranged in one or more linear arrays, for example, one or more linear array wherein the electrodes are arranged on a straight line in one dimension. Alternatively each of the plurality of electrodes may be arranged in a planar array, for example, in two dimensions to achieve a desired aperture shape such as rectangular, circular, square or another 2-dimensional planar shape. In a further example, each of the plurality of electrodes may be distributed and arranged on a non-planar surface to form a conformal array.

The spacing between electrodes can also be manipulated to achieve a desired directionality and/or aperture shape, and this may apply to linear, planar or conformal arrays. In one example, each one of the plurality of electrodes may be spaced uniformly apart from one another. In another example, one or more of the plurality of electrodes may be spaced non-uniformly apart from one another.

Manipulation of frequencies and/or relative phases and/or relative amplitudes of the stimulating signal can provide a further degree of design freedom in optimising aperture shape and directionality.

DESCRIPTION OF FIGURES

Preferred embodiments of the present invention will now be described with reference to the accompanying drawings, in which:

FIG. 1 indicates a plurality of electrodes such as those marked (1) and (3) exposed to a fluid. In this configuration, a potential has been applied across two electrodes marked (1), and the potential will be measured at the remaining electrodes including those marked (3). Electric field lines (2) will determine the potential at each electrode, and this will be influenced by impinging acoustic waves which will change the density and thus the local electrical properties which will in turn change the voltages across the array.

Figure 1:
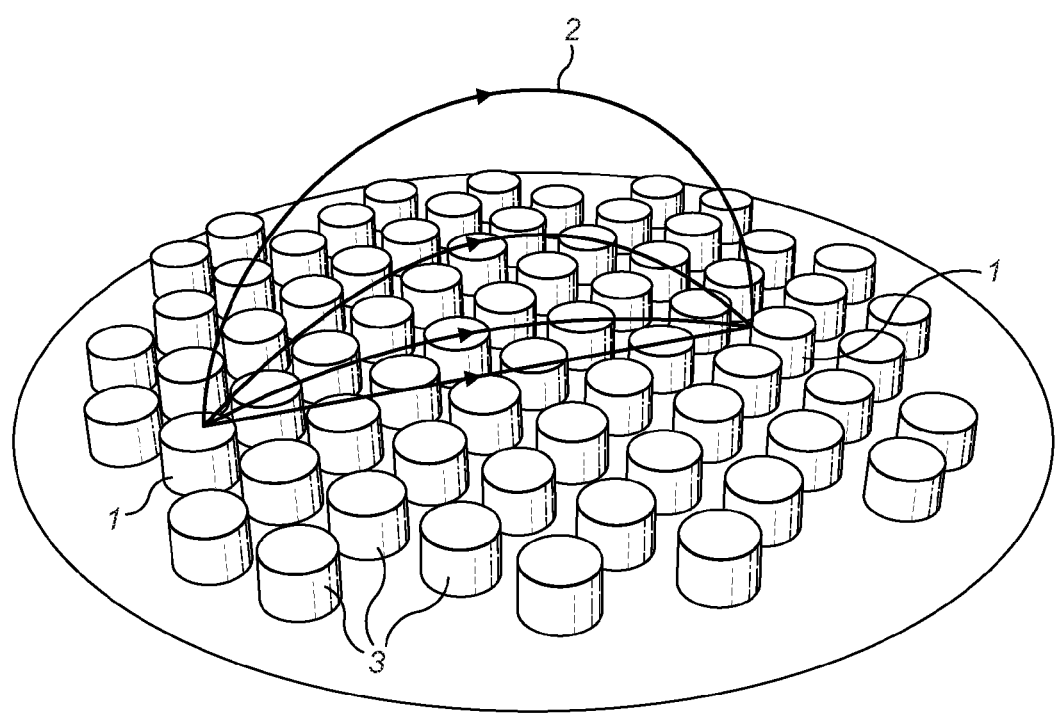
FIG. 1 shows a plurality of electrodes in accordance with an embodiment of the present invention.

In a preferred embodiment of the present invention, the following method steps may be used with reference to the apparatus of FIG. 1:

1. Placing a plurality of electrodes on a surface exposed to a fluid;
2. Stimulating a subset of the electrodes (1) at a plurality of carrier frequencies such that each electrode has a unique carrier frequency (or a combination of unique carrier frequencies);
3. Measuring the electrical potentials at the relevant carrier frequencies relative to some common potential at another subset of electrodes (3);
4. Repeating the stimulus and measurement steps as necessary with other subsets of electrodes and/or at different carrier frequencies;
5. Processing the measured data using EIT techniques to provide an acoustic map of the acoustic field at the required acoustic frequencies.

Figure 2:
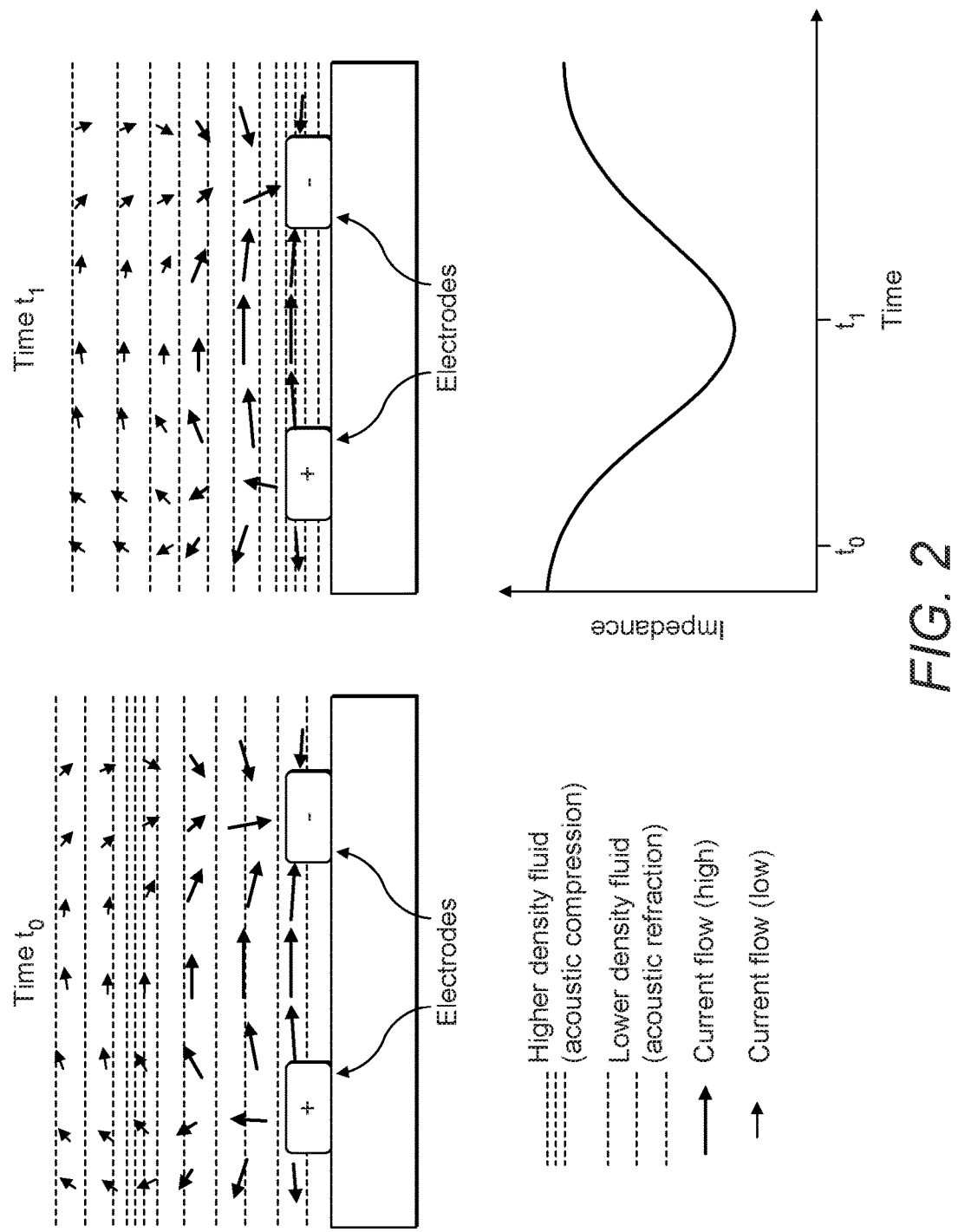
FIG. 2 shows the change in impedance across an electrode pair in response to an exemplary changing acoustic field.

FIG. 2 indicates an acoustic compression moving towards two sensing electrodes from time $t_0$ to time $t_1$. This influences the electric fields, causing some change in the impedance measured across the electrodes between time $t_0$ and $t_1$.

The following are clauses indicating preferred aspects according to the present disclosure.

1. A method of producing an electrical impedance tomographic image of an acoustic field within a fluid, comprising the steps of:
   positioning a plurality of electrodes within a fluid;
   applying an electrical signal across a subset of electrodes using different carrier frequencies and measuring the electrical potential at a subset of the electrodes;
   successively repeating the step of applying and measuring electrical signals, with different subsets of electrodes and/or at different carrier frequencies;
   processing the measured data to provide an acoustic map of the acoustic field at the required acoustic frequencies.
2. A method as in clause 1, whereby the impedance between electrodes is measured across a range of frequencies to compensate for global longer term trends in the electrical environment that are not related to the acoustic field, including temperature, pressure, chemical composition, electrode composition and surface effects.
3. A method as in clause 1 whereby the electrical impedance is measured only across a single electrode pair to provide a 1 dimensional measurement of acoustic signal strength across the electrode pair, where the signal strength is a function of the electrical impedance.
4. A method as in clause 1, whereby the electrodes are closely spaced conductive and non-corrosive materials such as carbon fibre which can be flush or conformal to the surface of the measurement platform.
5. A method as in clause 1, whereby the carrier frequencies are selected such that the electrical properties of the measurement fluid either do not change significantly over the range of carrier frequencies, or that the change with frequency is known.
6. A method as in clause 1, whereby the tomographic images produced also include the detection and identification of non-acoustic articles and effects.
7. A method as in clause 1, whereby instead or as well as the variation in frequency, the relative phase is varied across electrodes.

The invention claimed is:

1. A method for producing an electrical impedance tomographic image of an acoustic field within a fluid, comprising the steps of:
   a) positioning a plurality of electrodes within a fluid;
   b) applying an electrical signal to each electrode within a first subset of electrodes, wherein the electrical signal applied to each electrode has a different carrier frequency and/or phase;
   c) measuring the electrical potential at each electrode within a second subset of electrodes;
   and d) processing the measured data to provide an acoustic map of the acoustic field at the required acoustic frequencies.
2. A method as in claim 1, wherein the electrical signal(s) are applied substantially simultaneously to all of the electrodes in the first subset of electrodes in step (b), and/or the electrical potential at all of electrodes in the second subset of electrodes are measured substantially simultaneously in step (c).
3. A method as in claim 1, wherein the method further comprises calculating the electrical impedance between at least one pair of electrodes, and preferably between a plurality of pairs of electrodes, wherein a first electrode of the or each pair is selected from the first subset and a second electrode of the or each pair is selected from the second subset.
4. A method as in claim 1, wherein the method further comprises repeating steps (b) and (c) over a different first and second subset of electrodes respectively.
5. A method as in claim 1, wherein the method further comprises repeating steps (b) and (c) using different carrier frequencies and/or phases at step (b).
6. A method as in claim 1, wherein the impedance between electrodes is measured across a range of frequencies to compensate for global longer term trends in the electrical environment that are not related to the acoustic field, such as temperature, pressure, chemical composition, electrode composition and surface effects.
7. A method as in claim 1, wherein the electrodes comprise conductive and non-corrosive materials such as carbon fiber.
8. A method as in claim 1, wherein the electrodes are positioned on a measurement surface and are flush or conformal to the surface.
9. A method as in claim 1, wherein the different carrier frequencies and/or phases in step (b) are selected such that the electrical properties of the measurement fluid either do not change significantly between the different carrier frequencies and/or phases, or that the change with frequency and/or phases is known.
10. A system for producing an electrical impedance tomographic image of an acoustic field within a fluid using the method of claim 1, comprising a plurality of electrodes, a signal generator adapted to perform step (b), a device adapted to perform step (c), and a processor adapted to perform step (d).
11. A system as in claim 10, wherein each of the plurality of electrodes may be arranged in one or more linear arrays.
12. A system as in claim 10, wherein each of the plurality of electrodes may be arranged in a planar array.

13. A system as in claim 10, wherein each of the plurality of electrodes may be distributed and arranged on a non-planar surface to form a conformal array.

14. A system as in claim 10, wherein each one of the plurality of electrodes may be spaced uniformly apart from one another.

15. A system as in claim 10, wherein one or more of the plurality of electrodes may be spaced non-uniformly apart from one another.

16. A method for producing an electrical impedance tomographic image of an acoustic field within a fluid, comprising the steps of:
   a) positioning a plurality of electrodes within a fluid;
   b) applying an electrical signal to each electrode within a first subset of electrodes, wherein the electrical signal applied to each electrode has either or both a different carrier frequency and phase;
   c) measuring the electrical potential at each electrode within a second subset of electrodes;
   and d) processing the measured data to provide an acoustic map of the acoustic field at the required acoustic frequencies,
   wherein the first and second subsets each comprise only a single electrode and the electrical impedance is measured across the resulting electrode pair to provide a one-dimensional measurement of acoustic signal strength across the electrode pair, and wherein the signal strength is a function of the measured electrical impedance.

17. A method as in claim 16, wherein the method further comprises repeating steps (b) and (c) using either or both different carrier frequencies and phases at step (b).

18. A method as in claim 16, wherein the impedance between electrodes is measured across a range of frequencies to compensate for global longer term trends in the electrical environment that are not related to the acoustic field, such as temperature, pressure, chemical composition, electrode composition and surface effects.

19. A method as in claim 16, wherein either or both the different carrier frequencies and phases in step (b) are selected such that the electrical properties of the measurement fluid either do not change significantly between either or both the different carrier frequencies and phases, or that either or both the change with frequency and phases is known.

20. A system for producing an electrical impedance tomographic image of an acoustic field within a fluid using the method of claim 16, comprising a plurality of electrodes, a signal generator adapted to perform step (b), a device adapted to perform step (c), and a processor adapted to perform step (d).

* * * * *